(12) United States Patent
Gelissen et al.

(10) Patent No.: US 10,582,881 B2
(45) Date of Patent: Mar. 10, 2020

(54) SENSOR SYSTEM AND METHOD FOR DETERMINING A BREATHING TYPE

(71) Applicant: KONINKLIJKE PHILIPS N.V., Eindhoven (NL)

(72) Inventors: Jozef Hubertus Gelissen, Herten (NL); Cornelis Harm Taal, Utrecht (NL); Gerard De Haan, Helmond (NL); Mark Josephus Henricus Van Gastel, Tilburg (NL); Anjo Peeters, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 16/323,823

(22) PCT Filed: Aug. 18, 2017

(86) PCT No.: PCT/EP2017/070977
§ 371 (c)(1),
(2) Date: Feb. 7, 2019

(87) PCT Pub. No.: WO2018/033640
PCT Pub. Date: Feb. 22, 2018

(65) Prior Publication Data
US 2019/0209045 A1 Jul. 11, 2019

(30) Foreign Application Priority Data
Aug. 18, 2016 (EP) ..................................... 16184769

(51) Int. Cl.
*A61B 5/00* (2006.01)
*A61B 5/08* (2006.01)
(Continued)

(52) U.S. Cl.
CPC .......... *A61B 5/0816* (2013.01); *A61B 5/0205* (2013.01); *A61B 5/02416* (2013.01);
(Continued)

(58) Field of Classification Search
CPC . A61B 5/0816; A61B 5/7278; A61B 5/02416; A61B 5/0205; A61B 5/0295
See application file for complete search history.

(56) References Cited

U.S. PATENT DOCUMENTS 8,721,555 B2 5/2014 Westbrook et al.
9,002,427 B2 4/2015 Tupin, Jr. et al.
(Continued)

FOREIGN PATENT DOCUMENTS

WO 2014140978 A1 9/2014

OTHER PUBLICATIONS

Karlen, W. et al., "Estimation of Respiratory Rate From Photoplethysmographic Imaging Videos Compared to Pulse Oximetry", IEEE Journal of Biomedical and Health Informatics, vol. 19, No. 4, Jul. 2015.

(Continued)

*Primary Examiner* — Charles A Marmor, II
*Assistant Examiner* — David Joseph Fernandez-Fidalgo

(57) ABSTRACT

A sensor system is for determining a breathing type of a subject. It has first and second electromagnetic radiation (e.g. optical) sensors, for example PPG sensors. The sensors are for application to the skin of the subject at different sensor locations. The signals from the first and second sensors are analyzed to determine if there is predominantly a first breathing type (e.g. chest breathing) or predominantly a second breathing type (e.g. belly breathing), or a mixture of the first and second breathing types.

10 Claims, 2 Drawing Sheets

(51) Int. Cl.
  *A61B 5/0205* (2006.01)
  *A61B 5/024* (2006.01)
  *A61B 5/0295* (2006.01)
  *A61B 5/113* (2006.01)
  *A61B 5/1455* (2006.01)

(52) U.S. Cl.
  CPC .......... *A61B 5/6824* (2013.01); *A61B 5/6829* (2013.01); *A61B 5/7264* (2013.01); *A61B 5/7278* (2013.01); *A61B 5/0295* (2013.01); *A61B 5/113* (2013.01); *A61B 5/14552* (2013.01); *A61B 2562/0238* (2013.01)

(56) References Cited

U.S. PATENT DOCUMENTS

| | | |
|---|---|---|
| 9,044,558 B2 | 6/2015 | Baker, Jr. et al. |
| 2011/0060215 A1 | 3/2011 | Tupin, Jr. et al. |
| 2014/0303503 A1 | 10/2014 | Rocque et al. |
| 2015/0101609 A1 | 4/2015 | Melker et al. |

OTHER PUBLICATIONS

Allen, J. et al., "Similarity in bilateral photoplethysmographic peripheral pulse wave characteristics at the ears, thumbs and toes", Physiol. Meas. 21, pp. 369-377, 2000.

Van Gastel, Mark et al., "Robust Respiration Detection from remote PPG", Optical Society of America, 2015.

Nitzan, M. et al., "Pattern of respiratory-induced changes in fingertip blood volume measured by light transmission", J. Biomedical Science and Engineering, 2011, 4, 529-534.

Enomoto, T. et al., "Dynamic Indices of Preload", Crit Care Clin, 26, (2010) 307-321.

Nilsson, L. et al., "Respiratory variations in the reflection mode photoplethysmographic signal. Relationships to peripheral venous pressure", Bio-Optics in Medicine, Med. Biol. Eng. Comput., 2003, 41, 249-254.

Stromberg, J. et al., "Influence of Tidal Volume and Thoraco-Abdominal Separation on the Respiratory Induced Variation of the Photoplethysmogram", Journal of Clinical Monitoring and Computing, 575-581, 2000.

SENSOR SYSTEM AND METHOD FOR DETERMINING A BREATHING TYPE

CROSS-REFERENCE TO PRIOR APPLICATIONS

This application is the U.S. National Phase application under 35 U.S.C. § 371 of International Application No. PCT/EP2017/070977, filed on 18 Aug. 2017, which claims the benefit of European Patent Application No. 16184769.4, filed on 18 Aug. 2016. These applications are hereby incorporated by reference herein.

FIELD OF THE INVENTION

The present invention relates to a sensor system for determining a breathing type.

BACKGROUND OF THE INVENTION

Respiration sensors for monitoring breathing rates and patterns are well known.

One non-invasive way to measure respiration rate is to use photoplethysmograph (PPG) sensors. These measure volumetric changes of a body. Amongst the vital signs that can be retrieved from the PPG signal are pulse rate, arterial oxygen saturation, and respiration rate.

A pulse oximeter is a common example of a PPG-based sensor. While the purpose of such a sensor is to obtain a measure of blood oxygen saturation, it also detects changes in blood volume in the skin, and thereby performs PPG sensing. By detecting changes in blood volume, a cyclic signal corresponding to the pulse is obtained. Furthermore, this higher frequency pulse rate signal is modulated over a lower frequency signal which tracks the respiration rate. Thus, with suitable filtering of the PPG signal, both pulse rate and respiration rate signals can be obtained. PPG sensors, such as pulse oximeters, are thus commonly used to provide a measure of the pulse rate and respiration rate.

A PPG sensor for example contains at least one LED, and one light sensor. The LED and sensor are placed such that the LED directs light into the skin of the user, which is reflected or transmitted, and detected by the sensor. The amount of reflected/transmitted light is determined by, amongst others, the perfusion of blood within the skin.

The PPG system for example includes a red LED, a near-infrared LED, and a photodetector diode. The sensor is typically configured with the LEDs and photodetector diode directly on the skin of the patient, typically on a digit (finger or toe) or earlobe.

Other places on the patient may also be suitable, including the forehead, the nose or other parts of the face, the wrist, the chest, the nasal septum, the alar wings, the ear canal, and/or the inside of the mouth, such as the cheek or the tongue.

The LEDs emit light at different wavelengths, which light is diffused through the vascular bed of the patient's skin and received by the photodetector diode. The changing absorbance at each of the wavelengths is measured, allowing the sensor to determine the absorbance due to the pulsing arterial blood alone, excluding venous blood, skin, bone, muscle, and fat for example. The resulting PPG signal may then be analyzed.

In transmissive pulse oximetry, a sensor device is placed on a thin part of the patient's body. Reflectance pulse oximetry may be used as an alternative to transmissive pulse oximetry. This method does not require a thin section of the person's body and is therefore well suited to more universal application such as the feet, forehead and chest.

Respiration is essential to deliver fresh, oxygen rich air into the lungs from where it is transported via the blood to all body cells. Essentially, increasing the lung volume decreases the pressure in comparison to the ambient atmosphere and consequently, according to Boyle's Law, air flows into the lungs. By decreasing the lung volume, the opposite occurs and carbon dioxide flows out of the lungs along with the exhaled air.

The lung-volume variations may arise from muscles in two primary regions: the chest and the diaphragm (belly). Chest breathing occurs when the muscles in between the ribs contract, moving the rib cage to expand to the sides, front and back. Abdominal, or belly, breathing occurs when the diaphragm contracts, pressing the abdominal cavity downwards. The abdominal cavity cannot decrease but changes shape, moving the belly forward. In practice, all breathing involves some belly breathing, but not necessarily chest breathing.

When in rest, a normal respiratory cycle of a healthy subject starts with belly breathing and then turns into a combined belly and chest breath-motion. However, in stressful situations, people tend to breathe predominantly with the chest region in a relatively shallow and fast fashion. This type of breathing stimulates the sympathetic (fight flight) branch of the autonomic nervous system. In extreme cases, this causes hyperventilation, which lowers the pH-value of the blood (causing alkalosis).

Although breathing is controlled by the autonomic nervous system, a subject can voluntarily influence the breathing pattern and rate, and consequently suppress the fight/flight response by intentionally moving away from shallow, fast chest breathing to slower, deeper diaphragmatically breathing. Relaxation techniques typically aim at achieving this relaxing type of breathing.

Similarly, people suffering from chronic obstructive pulmonary diseases (COPD) or asthma can profit from these relaxation techniques to regain their breath.

Although PPG-sensors are ubiquitously used, and are capable of detecting the respiratory signal, they cannot distinguish between chest and abdominal breathing. For relaxation techniques the implies that the sensors can be used to check whether subjects are breathing slowly as suggested, but not whether they actually follow the advice to use predominantly belly breathing.

There is therefore a need for a sensor system which can distinguish between the two types of breathing.

SUMMARY OF THE INVENTION

Examples in accordance with a first aspect of the invention provide a sensor system for determining a breathing type of a subject, comprising:

a first electromagnetic radiation sensor having a first detector for association with the skin of the subject at a first sensor location;

a second electromagnetic radiation sensor having a second detector for association with the skin of the subject at a second sensor location; and a controller which is adapted to:

analyze the signals from the first and second detectors, wherein analyzing comprising:

determining a first measure from the first detector signal;

determining a second measure from the second detector signal;

determining a relationship between the first and second measures;

wherein the first and second measures each comprise:

(i) a measure of respiratory induced intensity variation (RIIV) for each detector signal relative to the amplitude at the pulse frequency; or (ii) a measure of respiratory induced pulse-amplitude variation (RIAV) for each detector signal relative to the amplitude at the pulse frequency; or.

(iii) a measure of respiratory induced intensity or pulse-amplitude variation for each detector signal relative to the DC-level at that detector; and determine from the analysis if there is predominantly a first breathing type or predominantly a second breathing type, or a mixture of the first and second breathing types.

By "association with" is meant the detector is applied to the skin or is remote from the skin, but in either case it is adapted to process a signal relating to the body tissue at that location.

These measures are respiration signal indicators. The relationship is for example a ratio or a difference or other combination of the two measures.

The invention is based on the recognition that some body sites show clearer breathing signals of a first type (e.g. chest breathing) whereas other body sites show stronger breathing signals of a second type (e.g. belly breathing). In particular, sensor signals measured from skin in lower body parts (with the subject in an upright position) are affected more by the pressure variations in the inferior vena cava (IVC), whereas the upper body parts shows sensor signals that are affected more by the pressure variations in the superior vena cava (SVC).

In particular, chest breathing is associated more with pressure variations in the SVC and belly breathing is associated more with pressure variations in the IVC.

By analyzing the two sensor signals, for example the relative signal strengths of the two sensor signals after each has already been processed to represent the respiration signal, the contributions of the two different breathing types may be determined.

The first and second sensors may be part of a sensor array. For example the sensing may be based on contact sensing using separate sensors at the body locations, or remote sensing using an image sensing approach.

The sensors may communicate with each other, or with a further external computation means using a wireless protocol.

The first and second measures for example each comprise a measure of respiratory induced intensity variation (RIIV) or a measure of respiratory induced amplitude variation (RIAV).

Thus, the measures may be based on amount of base-line modulation (intensity), or the amount of pulse-amplitude modulation, preferably normalized either to the pulse-amplitude or to the DC-level.

This normalization relative to the signal amplitude at the pulse frequency provides a fixed gain of the respiratory signal irrespective of the local perfusion of the skin.

In this way, the strength of the respiratory signal is measured relative to the strength of the pulse signal at the two body locations. The two body locations are respectively more affected by pressure in the SCV or the ICV, so that it becomes possible to discriminate between chest breathing (the first breathing type) and belly breathing (the second breathing type).

The first and second sensors for example operate in the wavelength interval between 400 nm and 1000 nm. The first and second sensors may each comprise a PPG sensor for which this wavelength interval is suitable.

Examples in accordance with another aspect of the invention provide a method for determining a breathing type of a subject, comprising:

associating a first electromagnetic radiation sensor having a first detector with the skin of the subject at a first sensor location;

associating a second electromagnetic radiation sensor having a second detector with the skin of the subject at a second sensor location;

analyzing the signals from the first and second detectors, wherein analyzing comprising: determining a first measure from the first detector signal;

determining a second measure from the second detector signal; and determining a relationship between the first and second measures, wherein the first and second measures each comprise:

(i) a measure of respiratory induced intensity variation (RIIV) for each detector signal relative to the amplitude at the pulse frequency; or (ii) a measure of respiratory induced pulse-amplitude variation (RIAV) for each detector signal relative to the amplitude at the pulse frequency; or (iii) a measure of respiratory induced intensity or pulse-amplitude variation for each detector signal relative to the DC-level at that detector; and determining from the analysis if there is predominantly a first breathing type or predominantly a second breathing type, or a mixture of the first and second breathing types.

This method enables simple electromagnetic (e.g. optical) based sensors to provide an indication of the type of breathing of a subject.

Using relative signals provides a normalization function.

The first breathing type for example comprises chest breathing and the second breathing type comprises belly breathing.

The method may comprise providing a first sensor location associated with (i.e. draining into) the Inferior Vena Cava, for example at the ankle, and providing a second sensor location associated with (i.e. draining into) the Superior Vena Cava, for example at the wrist.

The processing of sensor signals may be carried out in software.

BRIEF DESCRIPTION OF THE DRAWINGS

Embodiments of the invention will be described, by way of example only, with reference to the drawings, in which.

DETAILED DESCRIPTION OF THE EMBODIMENTS

The invention provides a sensor system for determining a breathing type of a subject. It has first and second electromagnetic (e.g. optical) sensors, for example PPG sensors. The sensors are for application to the skin of the subject at different sensor locations. The signals from the first and second sensors are analyzed to determine if there is predominantly a first breathing type (e.g. chest breathing) or predominantly a second breathing type (e.g. belly breathing), or a mixture of the first and second breathing types.

In one implementation, the system makes use of two PPG sensors.

Figure 1:
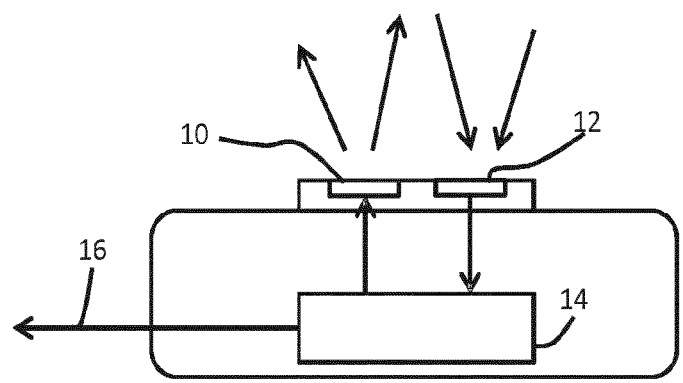
FIG. 1 shows a known PPG sensor.

FIG. 1 shows a known PPG sensor.

It comprises a light source 10 and an optical detector 12. The light source may comprise a single multi-wavelength light source, or multiple light units with different output wavelengths. The sensor has a processor 14 and it generates an output 16 in the form of a PPG signal which varies over time. The output may be provided in real time and/or it may be logged and stored as a trace over time during a monitoring period. The stored trace may then be analyzed after the monitoring period is over.

The PPG sensor for example comprises a pulse oximeter. The output 16 may be interpreted to provide a pulse rate, a respiration rate and an arterial oxygen saturation level, in known manner.

In one example, the invention is based on the combination of two PPG sensors which may be of the general type shown in FIG. 1.

Figure 2:
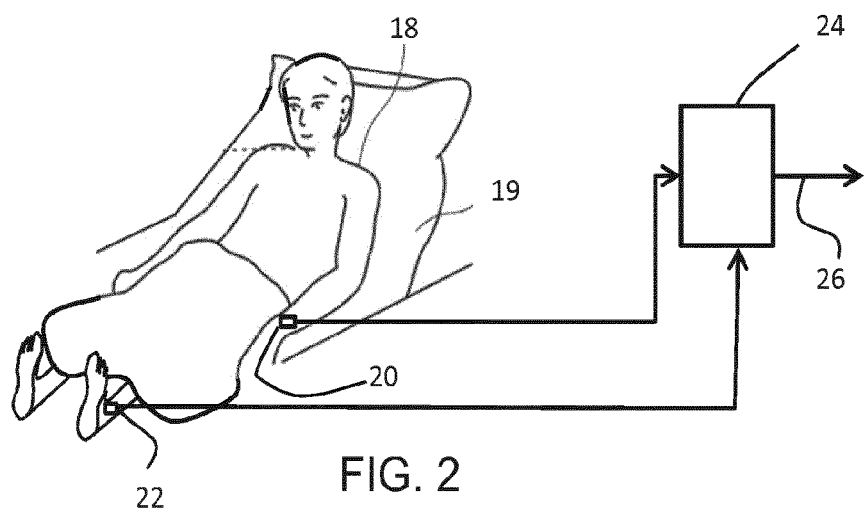
FIG. 2 shows a first example of system in accordance with the invention for determining different breathing types.

FIG. 2 shows a first example of system in accordance with the invention being used to monitor a subject 18 in a hospital bed 19.

The system has a first sensor 20 of the same type as shown in FIG. 1, thus having a first source of electromagnetic radiation and a first detector for application to the skin of the subject at a first sensor location. This first location is the wrist in the example shown.

A second sensor 22 is also of the same type as shown in FIG. 1, having a second source of electromagnetic radiation and a second detector for application to the skin of the subject at a second sensor location. The second location is the ankle in the example shown.

A controller 24 analyzes the signals from the first and second sensors and determines from the analysis if there is predominantly a first breathing type (chest breathing) or predominantly a second breathing type (belly breathing), or a mixture of the first and second breathing types.

Some body sites show clearer breathing signals relating to chest breathing whereas other body sites show stronger breathing signals relating to belly breathing. In particular, sensor signals measured from skin in lower body parts, particularly the lower limbs are affected more by the pressure variations in the inferior vena cava (IVC), whereas the upper body parts in particular the upper limbs show sensor signals that are affected more by the pressure variations in the superior vena cava (SVC).

By analyzing the two sensor signals, for example the relative signal strengths of the two sensor signals after each has already been processed to represent the respiration signal, the contributions of the two different breathing types may be determined.

In particular, the analysis may comprise measuring the strength of the respiratory signal relative to the strength of the pulse signal at the two body locations, and comparing these two strength signals.

Chest breathing is typically encountered during stressful situations and belly breathing is generally encountered during a relaxed state of the subject. The controller may in its simplest form provide an output 26 which is a binary indicator representing either chest or belly breathing. In a more detailed implementation, the degrees of belly breathing versus chest breathing may be indicated (e.g. a percentage).

The respiration signals received from the two body locations are preferably normalized. This normalization may comprise dividing the variations in the received signals at the respiratory rate by the amplitude of the variations at the pulse-rate. Other normalization approaches are possible, however, like dividing by the average value (DC) of the received signal at the detector. One benefit of the normalization is to obtain a fixed gain of the respiratory signal irrespective of the local perfusion of the skin. The normalization process is described in further detail below.

The sources of electromagnetic radiation for example operate in the wavelength interval between 400 nm and 1000 nm, where particularly a wavelength around 550 nm is included as the PPG signal is relatively strongest around this wavelength. More than one wavelength is preferably used to improve motion robustness of the device.

The sensors are in the example shown contact sensors, with the detector part in contact with the skin of the subject, while the skin region may be illuminated by an electromagnetic radiator which only needs to be mounted in close proximity to the skin.

The detectors of the sensors may instead form an image sensor array that may remotely detect the reflected/transmitted light from/through the skin of the subject at the two (or more) locations. Typically a camera remotely images the two different skin regions of the subject using either ambient or dedicated illumination.

The respiration signal is typically obtained as the low frequency component of the received detector signal, below the pulse frequency (e.g. 1 Hz). Alternatively, the respiration signal may be obtained the detector signals by extracting the relative strength of the amplitude modulation of the pulse signal at the respiratory rate.

It is for example disclosed in W. Karlen, A. Garde, D. Myers, C. Scheffer, J. Ansermino, and G. Dumont, "Estimation of respiratory rate from photoplethysmographic imaging videos compared to pulse oximetry," Biomedical and Health Informatics, IEEE Journal of, 19, 1331-1338 (2015) that the respiratory signal and the breathing rate (or breathing frequency) can be obtained from photoplethysmography (PPG) via three parameters:

- inter-beat intervals: inhalation increases heart rate, while after exhalation the frequency quickly drops, i.e. the pulse is FM-modulated with the respiratory signal.
- the DC part of the PPG signal: the DC component increases at inhalation and decreases at exhalation. This effect may be defined as baseline modulation, or respiratory induced intensity variation, RIIV.
- the AC part of the PPG signal: the AC component increases at inhalation and decreases at exhalation, i.e. the pulse-signal is amplitude modulated with the respiratory signal. This is often referred to as respiratory induced amplitude variation, RIAV.

The RIIV waveform has been found to be of particular interest for this application.

Figure 3:
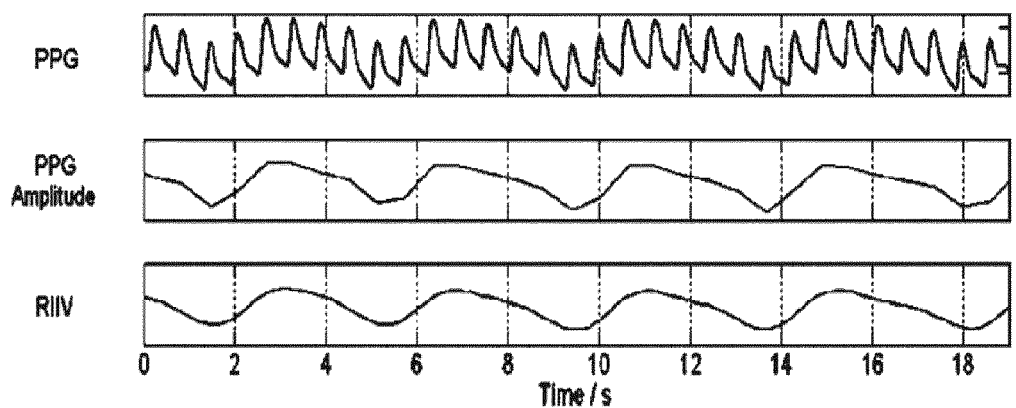
FIG. 3 shows a PPG signal, a PPG amplitude waveform and the RIIV waveform.

FIG. 3 shows a PPG signal, a PPG amplitude waveform and the RIIV waveform, which is a low pass filtered version of the PPG amplitude waveform. The PPG amplitude waveform is obtained by tracking the peaks of the PPG waveform and creating a linearly interpolated waveform.

The strength of the baseline variation as expressed by the RIIV signal has been found to depend strongly on the body location.

The PPG amplitude (AC amplitude) as well as DC values (area under the curve of the AC signal) varies depending on body site, which is why the normalization mentioned above is desired to compensate for this. The respiratory signal is for example normalized by the amplitude of the pulse signal. In this way, the baseline variation is expressed in relation to the magnitude of the pulse signal as seen in the PPG signal at that particular body location. The purpose is for the baseline variations as measured at each location to have equal significance in that a similar baseline variation magnitude results from a respiration signal. Other normalization approaches to achieve this aim may of course be considered. For example, an alternative normalization may use the DC-value of the reflected light. A signal may in effect be obtained relative to a DC level by taking the logarithm of the sensor signals. In this case, the resulting AC amplitudes are essentially the same as the amplitudes relative to the DC (normalized amplitudes).

When combining the two signals, a weighting may be applied, if needed. Thus one option is simply to measure a ratio of the normalized RIIV signals at the two locations. An alternative is to perform a scaling of one of the normalized signals first. The difference between the signals (or different between scaled/weighted signals) rather than a ratio may instead be used. The most appropriate signal combination of the two normalized RIIV signals may be obtained by previous experimentation.

More generally, any combination of signals (not necessarily RIIV signals) from the two body locations may be used as long as the combined signal has a strong correlation with the type of breathing. Thus regression analysis of experimental data may be used to determine a suitable signal combination which correlates with the breathing type. The example below is only one possible example.

The invention has been tested to provide proof-of-concept, and the results are presented below.

To verify the feasibility of the concept, PPG data obtained from a subject was analyzed, with the subject following a particular breathing protocol. The protocol prescribes breathing at a constant rate of 10 breaths/min with three types of breathing exercised sequentially: belly, chest and a combination of both. The combination is referred to as 'normal'.

Two identical PPG sensors were attached to the wrist and ankle locations of the subject and the PPG-signals were synchronously sampled with a sampling frequency of 128 Hz.

For each breathing modality, respiratory features were extracted from the PPG waveform in the form of the DC variation (respiratory induced intensity variation, RIIV).

An absolute RIIV variation was measured, determined by the amplitude at the breathing frequency in the frequency spectrum of the normalized PPG signal.

A relative variation was also measured, based on the absolute RIIV definition above, but scaled with respect to the amplitude at the pulse frequency as explained above.

For these features, the ratio between the signals gathered the wrist and ankle locations were then calculated, i.e.

RIIV_absolute_ratio=RIIV_absolute(wrist)/RIIV_absolute(ankle).

RIIV_relative_ratio=RIIV_relative(wrist)/RIIV_relative(ankle).

These values are presented in the table below. The ratio is expected to be to be higher the more chest breathing dominates.

| Type of Breathing | RIIV_absolute_ratio | RIIV_relative_ratio |
|---|---|---|
| Normal | 0.70 | 0.55 |
| Belly | 0.35 | 0.30 |
| Chest | 0.61 | 0.64 |

These results show that the relative RIIV measure provides a signal for which chest breathing gives the highest ratio, belly breathing the lowest ratio, while 'normal' breathing shows up in between these two. It also shows how the normalization improves the results.

An alternative measure is the AC variation (respiratory induced amplitude variation, RIAV). Again, an absolute value may be determined, for example as the standard deviation of the derivative of the peak-valley pairs. A relative value is similar to the absolute RIAV definition, but again scaled with respect to the cardiac pulse amplitude to correct for local variations in PPG strength.

The invention is of interest for both home healthcare as well as within the clinical environment. It can be used to help guide a user to achieve relaxed breathing, for example in the event of an asthma attack or other breathing difficulties.

The example above is based on the use of two contact sensors. Recently, non-contact, remote PPG (rPPG) devices (also called camera rPPG devices) for unobtrusive measurements have been introduced. Remote PPG utilizes light sources or, in general radiation sources, disposed remotely from the subject of interest. Similarly, also a detector, e.g., a camera or a photo detector, can be disposed remotely from the subject of interest. Therefore, remote photoplethysmographic systems and devices are considered unobtrusive and well suited for medical as well as non-medical everyday applications. This type of sensing may be used by the system of the invention, although remote PPG devices typically achieve a lower signal-to-noise ratio.

In this case the PPG sensors may for example make use of a camera flash as the optical source, and a camera image sensor as the sensor device. In this way, with a suitable application running on a mobile phone, the system can be implemented.

There may be more than two sensors, to provide additional information to be processed in order to determine the breathing type with greater accuracy.

Figure 4:
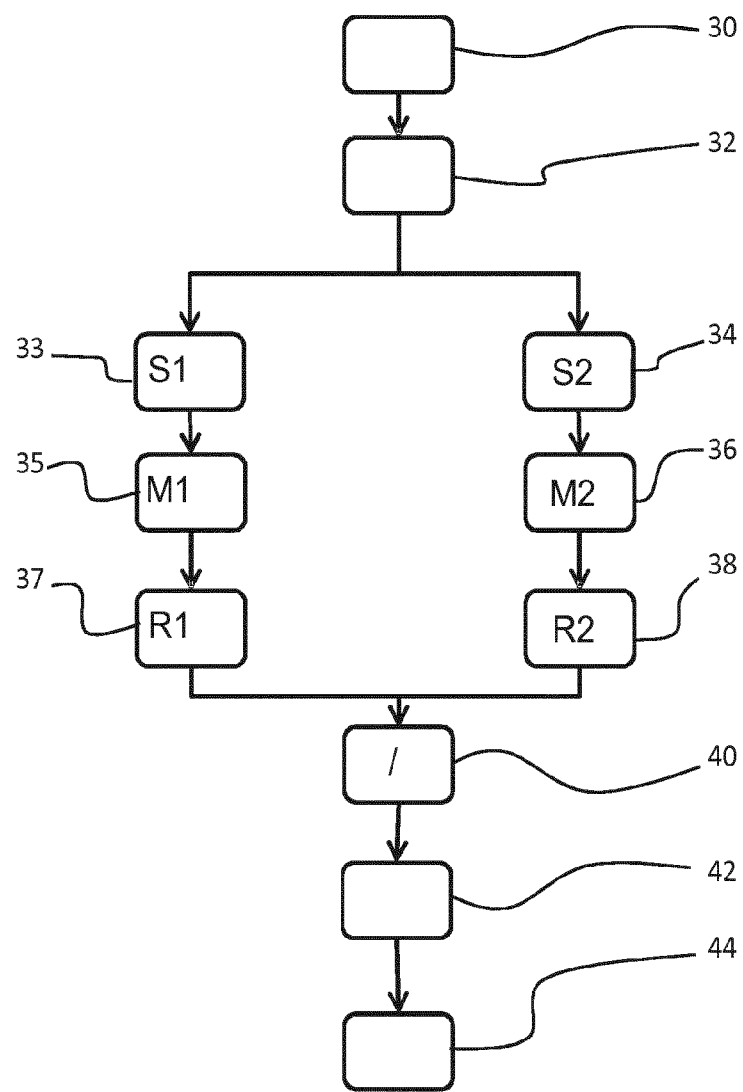
FIG. 4 shows a method for determining different breathing types.

FIG. 4 shows a method for determining a breathing type of a subject.

In step 30 a first sensor having a first source of electromagnetic radiation and a first detector is associated with the skin of the subject at a first sensor location. It may be applied to the skin or it may be arranged for remotely monitoring the body at that location.

In step 32, a second sensor having a second source of electromagnetic radiation and a second detector is associated with the skin of the subject at a second sensor location.

In step 33 the first second signal S1 is obtained. It is converted to a measure of the respiration trace in step 35 for example by low pass filtering or other signal processing to obtain a first measure M1 of the respiration. This measure is normalized in step 37 to provide a relative value R1.

In step 34 the second signal S2 is obtained. It is converted to a measure of the respiration trace in step 36 for example by low pass filtering or other signal processing to obtain a second measure M2 of the respiration. This may be the respiratory induced intensity variation (RIIV). This measure is normalized in step 38 to provide a relative value R2.

The two relative values are processed in step 40, for example to find a ratio, or a weighted ratio, or other linear or non-linear combination of the signals (also may be referred to as a relationship). Form this processing, it is determined in step 42 if there is predominantly a first breathing type or predominantly a second breathing type, or a mixture of the first and second breathing types.

An output is provided in step 44.

The first breathing type comprises chest breathing and the second breathing type comprises belly breathing.

The signal processing may be implemented by a computer program which forms or is part of the controller 24. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

The examples above make use of PPG measurements. The electromagnetic sensors are used to obtain a respiration trace, and do not need to output photoplethysmography signals. Thus, other reflectance or transmittance sensors may be used.

Two breathing types are discussed above. Thoracic (chest) and diaphragmatic (belly) breathing are the two most common types of breathing. There is also clavicular breathing, which is breathing into the top third of the lungs and no deeper. Clavicular breathing is accomplished by raising the collarbone (clavicle) and shoulders during the inhalation and keeping the rest of the torso motionless. Clavicular breathing is the most shallow type of breathing. Clavicular breathing may also be distinguishable, or else it may be identified as chest breathing.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A sensor system for determining a breathing type of a subject, comprising:
   a first electromagnetic radiation sensor having a first detector for association with the skin of the subject at a first sensor location;
   a second electromagnetic radiation sensor having a second detector for association with the skin of the subject at a second sensor location; and
   a controller which is adapted to:
   analyze the signals from the first and second detectors, wherein analyzing comprises:
   determining a first measure from the first detector signal;
   determining a second measure from the second detector signal;
   determining a relationship between the first and second measures;
   wherein the first and second measures each comprise:
   (i) a measure of respiratory induced intensity variation relative to the amplitude at the pulse frequency; or
   (ii) a measure of respiratory induced pulse-amplitude variation relative to the amplitude at the pulse frequency; or
   (iii) a measure of respiratory induced intensity or pulse-amplitude variation relative to the DC-level at that detector; and
   determine from the analysis if there is predominantly a first breathing type or predominantly a second breathing type, or a mixture of the first and second breathing types.

2. A system as claimed in claim 1, wherein the first and second electromagnetic radiation sensors operate in the wavelength interval between 400 nm and 1000 nm.

3. A system as claimed in claim 1, wherein the first and second electromagnetic radiation sensors each comprise a PPG sensor.

4. A system as claimed in claim 1, wherein the first breathing type comprises chest breathing and the second breathing type comprises belly breathing.

5. A method for determining a breathing type of a subject, comprising:
   associating a first electromagnetic radiation sensor having a first detector with the skin of the subject at a first sensor location;
   associating a second electromagnetic radiation sensor having a second detector with the skin of the subject at a second sensor location;
   analyzing the signals from the first and second detectors, wherein analyzing comprises:
   determining a first measure from the first detector signal;
   determining a second measure from the second detector signal; and
   determining a relationship between the first and second measures, wherein the first and second measures each comprise:
   (i) a measure of respiratory induced intensity variation relative to the amplitude at the pulse frequency; or
   (ii) a measure of respiratory induced pulse-amplitude variation relative to the amplitude at the pulse frequency; or
   (iii) a measure of respiratory induced intensity or pulse-amplitude variation relative to the DC-level at that detector; and determining from the analysis if there is predominantly a first breathing type or predominantly a second breathing type, or a mixture of the first and second breathing types.

6. A method as claimed in claim 5, comprising providing outputs from the first and second sources of electromagnetic radiation in the wavelength interval between 400 nm and 1000 nm.

7. A method as claimed in claim 5, wherein the first breathing type comprises chest breathing and the second breathing type comprises belly breathing.

8. A method as claimed in claim 7, comprising providing a first sensor location associated with the Superior Vena Cava and providing a second sensor location associated with the Inferior Vena Cava.

9. A method as claimed in claimed in claim 8, wherein the first sensor location is the wrist and the second sensor location is the ankle.

10. A computer program product comprising a non-transitory computer readable medium, wherein the computer program product comprises computer readable code which is adapted, when run on a computer, to receive signals from a first electromagnetic radiation sensor associated with the skin of the subject at a first location and a second electromagnetic radiation sensor associated with the skin of the subject at a second location and to perform the steps of analyzing and determining of the method of claim 5.

* * * * *